United States Patent [19]

Lovoi

[11] Patent Number: 4,986,664
[45] Date of Patent: Jan. 22, 1991

[54] SYSTEM AND PROCESS FOR CONTROLLED REMOVAL OF MATERIAL TO PRODUCE A DESIRED SURFACE CONTOUR

[75] Inventor: Paul A. Lovoi, Saratoga, Calif.

[73] Assignee: International Technical Associates, Santa Clara, Calif.

[21] Appl. No.: 180,208

[22] Filed: Apr. 11, 1988

Related U.S. Application Data

[63] Continuation-in-part of Ser. No. 862,285, May 12, 1986, Pat. No. 4,737,628, which is a continuation-in-part of Ser. No. 577,760, Feb. 7, 1984, Pat. No. 4,588,885.

[51] Int. Cl.$^5$ .................. G01B 11/24; B23K 26/00
[52] U.S. Cl. ........................... 356/376; 219/121.62; 219/121.68
[58] Field of Search ............... 219/121.61, 121.62, 219/121.67, 121.68, 121.69; 356/376, 377

[56] References Cited

U.S. PATENT DOCUMENTS

| | | | |
|---|---|---|---|
| 3,700,850 | 10/1972 | Lumley et al. | 219/121.62 |
| 4,504,727 | 3/1985 | Melcher et al. | 219/121.62 |
| 4,555,610 | 11/1985 | Polad et al. | 219/121.62 |
| 4,718,418 | 1/1988 | L'Esperance, Jr. | 219/121.68 |

*Primary Examiner*—Edward P. Westin
*Attorney, Agent, or Firm*—Thomas M. Freiburger

[57] ABSTRACT

A method and apparatus for controlling the milling of an ablatable material and the like from substrate is disclosed. Embodiments for controlling the milling of ablatable materials and the like by pulses of high intensity radiant energy are described. The control process is accomplished by generating an electronic signal representative of the substrate surface topology through use of a structured light or other three dimensional mapping system and feeding the signal to a system control unit. By applying pre-programmed criteria regarding the final desired surface to the generated electronic signal, an electronic reference signal indicative of the dimensional coordinates of the final desired surface may be generated. An ablatable coating is then applied to a height sufficiently above the final desired surface to permit a milling off of the excess coating to produce the desired final surface topology. In the milling process the mapping system is used as a real-time feedback control mechanism for directing a laser. By scanning the surface ahead of the laser, the mapping system generates a new electronic signal representative of the coated surface topology, and this signal is compared to the desired-topology reference signal. At each spot where the comparison indicates the coated surface is above the final desired surface, the controller will order the laser to fire upon that spot, and this is reiterated until the surface features fall within the prescribed limits.

17 Claims, 8 Drawing Sheets

SYSTEM AND PROCESS FOR CONTROLLED REMOVAL OF MATERIAL TO PRODUCE A DESIRED SURFACE CONTOUR

REFERENCE TO RELATED APPLICATION

This application is a continuation-in-part of application Ser. No. 862,285 filed May 12, 1986, now U.S. Pat. No. 4,737,628, which was a continuation-in-part of application Ser. No. 577,760, filed Feb. 7, 1984, now U.S. Pat. No. 4,588,885.

BACKGROUND OF THE INVENTION

The invention relates to the use of radiant energy for the selective and controlled removal of ablatable material from a substrate without removing or damaging the substrate, and more specifically to an improved method and apparatus for smoothing or shaping a surface to preselected limits.

Many industrial procedures require the removal of a material or materials from a substrate or from adjacent materials in order to achieve a smooth surface. The wide variety of techniques used to perform this task include mechanical grinding, scraping, and blasting with sand or other abrasives. All of these methods have the disadvantages of being labor intensive and imprecise.

In U.S. Pat. No. 4,588,885, there is disclosed an automatic laser paint removal system for removing paint and other coatings from metallic or other substrates through an electronic control process. The control is accomplished by illuminating the area of the paint and the like which is to be stripped and subjecting the light reflected therefrom to spatial spectral dispersion. The spatial spectral dispersion is sensed and an electronic signal representative thereof is generated. The generated electronic signal is compared to a pre-recorded electronic signal representative of the spatial spectral dispersion of the paint or other coating(s) which are to be removed. This comparison is made before each pulse of high intensity radiant energy, and the pulse is applied only upon such comparison resulting in a substantial match.

The paint removal system described has some relation to the present invention, in that a surface condition is monitored and a decision is made whether to fire a scanning laser beam at each small unit of area covered, based on information just obtained by the monitoring for that unit of area.

The sensor system disclosed in U.S. Pat. No. 4,588,885 provides information for control of the firing of the laser only via the material at the surface of the area being stripped. The patented system does not provide or utilize a contour sensing subsystem and it is unable to accomplish the objective of the present invention, i.e. to achieve a desired contour.

SUMMARY OF THE INVENTION

According to the method and apparatus of the invention, the smoothing or milling of a surface may include three-dimensional pre-mapping of the surface to be smoothed (or the substrate beneath the surface) with a structured light mapping system or other suitable system for determining surface contour, such as systems employing holography, speckel interferometry or laser backscatter techniques. The structured light mapping system may utilize a low-power line of laser light across the scan area of the surface to be mapped. This mapping subsystem provides information on the distance of the laser end effector from the surface, as well as surface contour information.

The line of light from the mapping system may be viewed by a solid state camera at an angle and location fixed relative to the line of light such that the line intersects a raster scan of the camera. At every position in the scan area, the height of the surface at that position causes the line of laser light to intersect the raster scan of the camera at a unique coordinate such that a height value for each position is electronically generated. This signal is then fed to a milling system control unit, and is stored so that the substrate base topology is known and can be used for later reference. A reference signal is then generated representing desired surface topology, based on preselected and computer-stored criteria on permissible slopes in the final surface.

The area to be smoothed is then filled or coated with an organic ablatable material, providing an overcoat which can be milled. The overcoat must be thick enough to be at or above the desired surface topology at every point. The mapping system will now be used as part of a real-time feedback control mechanism for directing the laser. By scanning the coated surface ahead of the laser, the mapping system generates a new electronic signal representative of the topology of the coated surface. The newly generated signal is compared to the reference signal (representing desired contour); and where the comparison indicates the height value of the coated surface is above a height value of the desired surface represented by the reference signal, a decision will be made to fire the laser at that particular spot. The controller will order the laser to fire when it reaches that spot. The laser itself will always be a few spots behind the scanning system. Each spot may be approximately one square centimeter in area.

While the laser is milling the area just scanned, the mapping system has indexed to a subsequent raster scan position and collects new data relative to surface height for that position. The controller again compares the height value of the generated signal with the height value of the reference signal at that position and makes a decision whether to fire the laser when the laser reaches that position in its raster.

After the laser has completed milling of a scan area, the mapping system then again scans the surface in real time to give an updated map and new firing orders to be executed by the laser. This procedure continues across an entire frame, with less and less firing of the laser, until the surface features fall within the prescribed limits.

A raster subsystem provides a mechanism by which the center position of each of the laser footprints in a raster pattern is shifted as to X and Y position for each milling sequence to allow the total energy delivered to an area to be smoothed out. The rastering may be accomplished by a high precision rotating replicate optics spinning mirror assembly, which will provide a highly accurate raster scan.

An example of the use of the laser milling system of the invention is in the smoothing of aircraft seam filling material. During the manufacture of aircraft, various sub-sections are assembled together. The joints between these various sections must be filled for a variety of reasons including maintainability, vulnerability and performance. The filling task usually involves a soft compliant material that will withstand the rigors of the aircraft flight environment as well as remain sufficiently compliant to the changing shape of the aircraft. This filled joint, whether it be a joint between sections or over rivet heads, knicks, scratches or other flaws, must then be smoothed to the aircraft profile as closely as possible. The claimed method and apparatus of this invention can be automated to accomplish the smoothing of ablatable material with a good deal of precision and can therefore efficiently replace prior art processes involving sanding, chemical smoothing, mechanical cutting and scraping and other techniques, which all suffer from being labor intensive and imprecise.

In another embodiment of the invention, an ultrasound mapping system may replace the structured light system and the need for premapping. The ultrasound system determines the thickness profile of the coating at each position by comparing sound waves reflected from the surfaces of both the coating and the underlying substrate Using this data, the system controller can then determine the desired contour and therefore the amount of material to be removed at each laser footprint, and can instruct the laser accordingly.

In another specific embodiment of the invention, wherein the system is used to form an aircraft surface which is smooth enough to avoid radar detection, a radar system with feedback can be used in conjunction with the mapping subsystem described above. Radar can be directed against a seam or other feature, before or after a spot on the feature has been burned by the laser to remove material, and the feedback from the laser can help determine whether and to what extent the objective of low radar profile has been achieved at that point. The radar feedback subsystem and the 3-D mapping system can also be used in conjunction with an expert system, for "learning" as the process progresses, regarding the nature of the features and end result sought. The expert system helps make decisions as to which direction to go, when a feature is not improving in smoothness, and will also fine-tune the system and the achieved result. The system can have inputs regarding a target or threshold acceptable level of radar invisibility, and the radar subsystem can confirm when these have been met. The above and other objects, advantages, features and characteristics of the invention will be understood from the following description of a preferred embodiment, considered along with the accompanying drawings.

DESCRIPTION OF THE PREFERRED EMBODIMENT

The invention described encompasses a technique for surface milling using a real-time feedback control mapping system in conjunction with a laser milling system.

Figure 1:
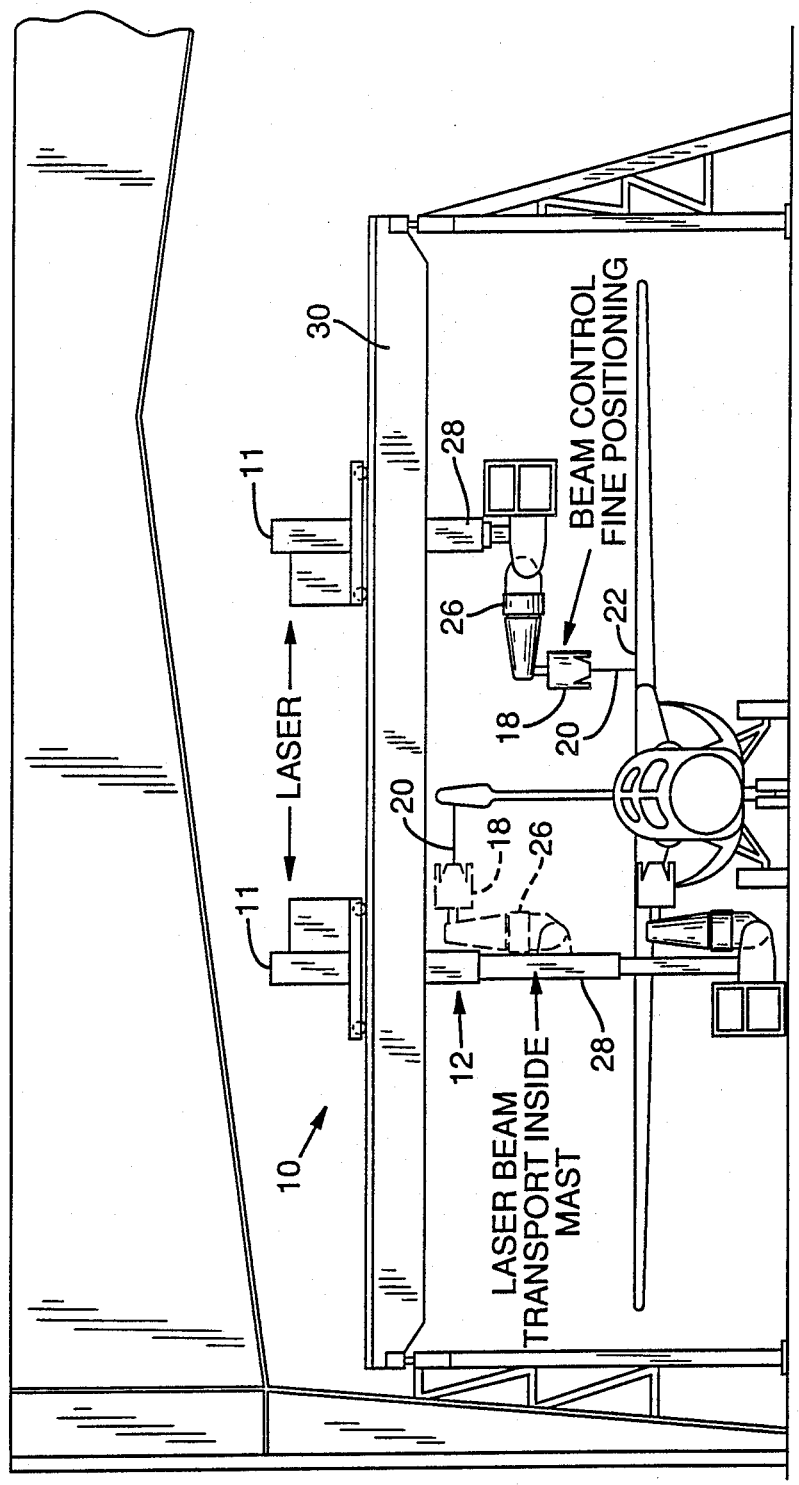
FIG. 1 is a conceptual drawing showing use of the invention in conjunction with aircraft manufacturing and maintenance.
Figure 2:
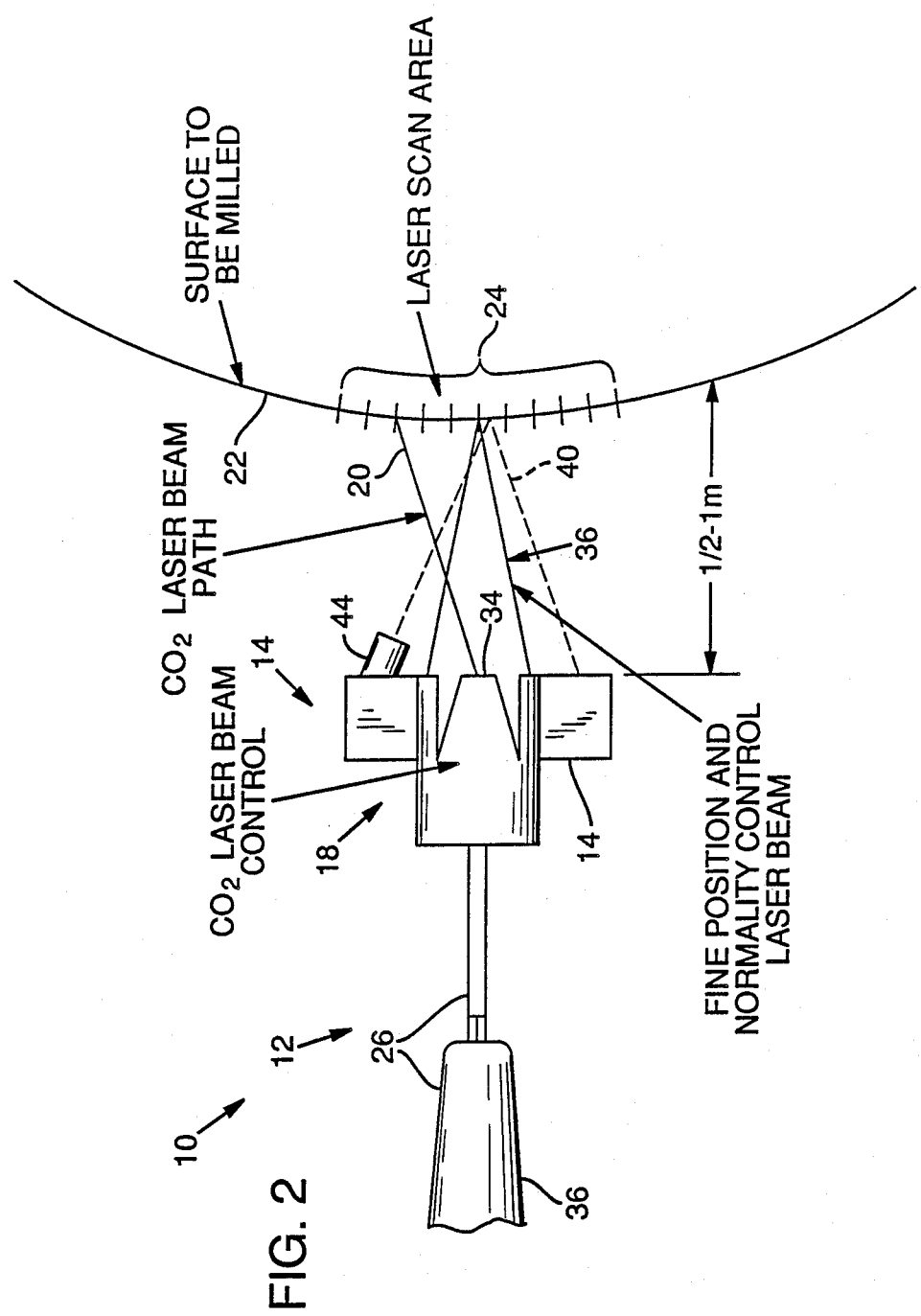
FIG. 2 is a conceptual drawing showing an example of a physical arrangement of a laser milling end effector of a robot apparatus, in relation to the surface to be milled, in accordance with the system of the invention.

FIGS. 1 and 2 show a preferred embodiment of the invention adapted to perform automatic surface milling operations in conjunction with the construction or maintenance of an aircraft. The system is adaptable to many other uses involving surface smoothing of an ablatable material.

The laser milling system 10 of the invention includes a high powered laser 11 (FIG. 1), a beam delivery subsystem 12, a mapping subsystem generally indicated as 14, and a rastering subsystem. A laser beam control and fine pointing system, generally identified at 18, is shown with a beam 20 of radiant energy generated thereby impinging upon a target surface 22. The target surface 22 may be the outer surface of an airplane, for example (as indicated in FIG. 1), which has been coated with an ablatable material. The ablatable material, which may be an organic filler material which remains somewhat pliable such as typically used on aircraft, is to be milled in order to achieve a smooth surface.

In the preferred embodiment, the beam 20 is generated by a $CO_2$ laser 11 which produces radiant energy having a 10.6 micron wavelength with a high efficiency. However, a different type of laser may be more suitable for various specialized uses in which this invention may be applied.

The laser 11 may have either a pulsed or a continuous output. The material removal process of the invention has been shown to take off 100–200 micro-inches of material at a power of 5 joules per square centimeter, with a 20 micro-second long laser pulse. Using a pulsed output allows examination of the target before, between and after pulses for process control.

If the energy density and/or the pulse length is reduced, more pulses will be required to vaporize the full depth of a given layer of material, but finer control of the process will be possible. If the energy density and/or the pulse length is increased, fewer pulses will tend to be required to remove the full depth of a given layer, but control of the process is more coarse.

The actual removal rate at a given pulse rate and energy density will be determined by the beam size (footprint area). For a given laser, the energy density selected will determine the size of the footprint area and the average power of the laser will determine the maximum pulse rate. For the purposes of this discussion it will be assumed that the beam 20 of the laser 11 provides a footprint of one square centimeter having an energy density of five joules per square centimeter, although actual values selected for each application may be quite different. It will be further assumed, again only for demonstration, that the laser 11 is capable of providing twenty microsecond pulses at a maximum pulse rate of about 1000 Hz. The realized laser pulse rate and thus the achieved removal rate is determined by several items other than the maximum laser pulse rate. These limits include substrate heating, and smoke and residue clearing, as well as control factors.

Substrate heating can to be the most serious limitation. The substrate heating rates will differ with both footprint area and substrate material. However, as will be more fully discussed hereinafter, substrate heating may be reduced by rastering of the laser beam, and the applicant's invention is specifically adapted to accommodate such rastering. In other words, the laser beam 20 need not be repeatedly pulsed on a single location but may be moved after each pulse to an adjacent location to define a raster. The beam can be returned to a given location after five or ten pulses thus giving each location five or ten times longer to cool before the beam is again impinged on that spot. Such rastering allows a much higher pulse rate and the average removal time may be five or ten times as fast as the removal rate attainable by repeatedly impinging the beam at a given location, because of the substrate heating limitation.

As will be described more fully below, according to this embodiment of the apparatus of FIG. 1 and 2, the beam 20 of the laser will be deflected to cover the laser scan area 24 in a raster. Thus a one square centimeter footprint of the beam 20 will be sequentially pulsed from left to right, for example, over the area 24 with each footprint impinging on a successive area. Other scanning sequences could be used and, if the laser has sufficient power, it could be operated continuously (as opposed to pulsed) during a continuous raster over the area 24. Thus the laser 11 will include an appropriate mirror system or other means for deflecting the beam 20 to cover the area 24 in one square centimeter increments. Such beam rastering systems are well known and the particular implementation of the rastering does not form a part of the invention.

In addition to removing the material, the laser has a built in smoothing effect in that small surface structures, on the order of one half centimeter and less, tend to be smoothed by a selective volatilization process. This can be explained as follows. The laser removes material by heating it to a point where the material volatizes and in doing so decomposes into small chain hydrocarbons and gas. Since this process is basically one of laser energy absorption at the surface with subsequent heat conduction through the material, parts of the surface area being smoothed that are raised above the average terrain have less ability to conduct heat away than do materials which lie in flat areas. These raised areas heat more rapidly and stay hot longer than do the flat or recessed areas and are therefore more susceptible to being removed. By this process the laser smooths the surface from small structured details. Test samples have shown that the laser is capable of leaving a 100 microinch or better finish. Smooth surfaces in polysulfide, for example, have a uniform mat appearance.

In the preferred embodiment shown in FIG. 1, the beam delivery subsystem 12 is employed to convey the laser beam 20 from the laser 11 to a precise location on the target surface 22. The beam delivery system comprises a robotic subsystem 26, a laser beam transport subsystem 28, and the beam control and fine pointing subsystem 18. The entire beam delivery subsystem 22 travels on overhead girders 30 in such a way that it can be moved laterally or longitudinally with reference to the structure in order to position the beam control 18 over the desired location.

Referring to FIG. 2, the fine pointing and control subsystem 18 is shown integrated with the $CO_2$ laser end effector 34 and the structured light mapping system 14. Such assembly can be built in a unit having a volume of less than one-half cubic foot and weighing about ten pounds. The unit can be carried by a robotic arm 36 or other movable structure$and should be between about one-half and $1\frac{1}{2}$ meters from the surface 22 of the target in use. The laser beam 20 should be substantially normal to the surface 22 of the target with a beam 40 from the structured light mapping system 14 and a camera 44 of the mapping system nearly normal to the surface 22 of the target.

The laser beam control and fine pointing system 18 provides the fine control signals to the robotic subsystem 26 in order to maintain the end effector 34 normal to the surface 22 and at a proper distance for correct laser focus. This subsystem may produce a structured light pattern made from rotating the laser beam to form a cone at the surface 14. The structured light pattern intersects the surface 22 to forming generally a circle. When the structured light pattern is brought to a single point on the surface, the system is at the correct focal distance. The shape of the "circle," when the system is slightly off focus, is determined by the angle of the end effector 34 relative to the surface. This measurement is thereby used to correct the system for normality and distance.

The laser beam 20 is then conducted from the laser 11 by way of the beam transport subsystem 28 which typically comprises hollow tubes with precision bearings mounted on each end. Mirrors mounted within the tubes redirect the beam in such a way that as the joint moves, the laser beam is maintained down the center line of both the incoming and outgoing segments. Such beam delivery systems are commercially available.

The robotics subsystem 26 must be of the type capable of providing collision avoidance to prevent the beam delivery system 12 from contacting the target structure 22. The robotics subsystem 26 must also instruct the laser 11 on the general areas that should not be milled. One such robotic system is manufactured by CIMCORP of Minneapolis, Minn., and the present laser milling system can be implemented in conjunction with this robotics system.

The robotic system 26 also must be capable of tolerating variations and changes in the target structure 22, such as movement of the target structure in relation to the milling system 10. One method of accommodating for such changes is by coordinate transformation. By using fiducial points on the structure as benchmarks, the milling system can be reoriented to a precise location with respect to the structure by optical triangulation.

According to a preferred embodiment of this invention, the profile of the target surface 22 of the area to be milled will be ascertained prior to milling through the use of the structured light mapping system 14.

The structured light mapping system 14 may comprise a low powered laser beam scanning system that provides a line of laser light 40 across the scan area 24 of the target surface 22 the scan area 24 being apportioned into individual adjoining positions of approximately one square centimeter. The line of light 40 is viewed by the solid state camera 44 at an angle and location fixed relative to the line of light 40 such that the line intersects a raster scan of the camera. At every position in the scan area 24, the height of the surface at that position causes the line of laser light 40 to intersect the raster scan of the camera at a unique coordinate, i.e. at a unique position in the camera's field which reflects the surface height. Thus, with these unique coordinates a height value for each position is electronically generated. Each of these coordinate points makes up one data point in the mapping process, thereby providing the necessary input to construct a detailed profile of the target surfaced. The data are input to a milling control system 46 indicated generally in block diagram form in FIG. 5, so that the pre-existing surface profile is now known and stored.

Figure 5:
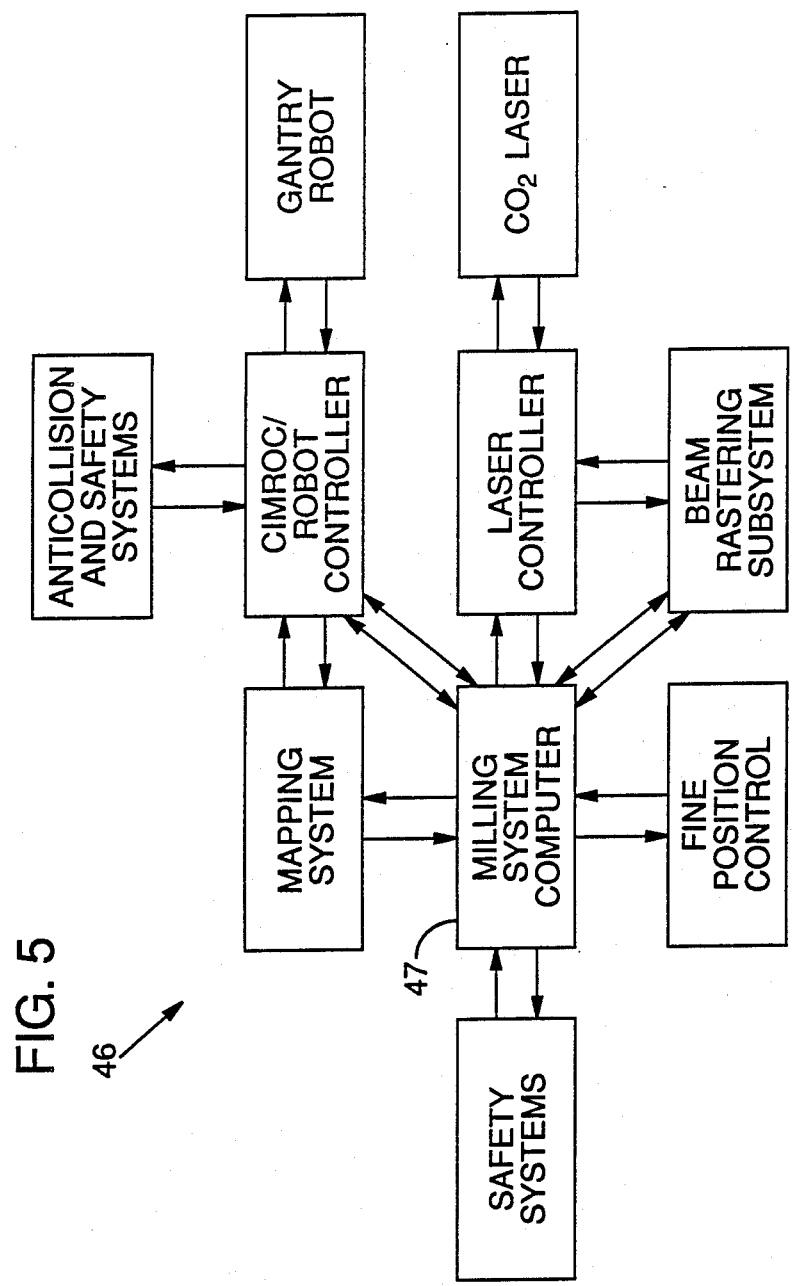
FIG. 5 is a general block diagram of the system's components according to a preferred embodiment of the invention.

Pre-programmed criteria regarding the desired surface profile, i.e. maximum permissible slopes in the final desired surface, are applied to the data representing the substrate topology, in the computer 47 indicated in FIG. 5. The computer also assumes a certain minimum thickness of overcoat. Using the selected criteria and the known substrate topology, the computer outlines a final desired surface profile and generates a new reference signal indicative of a desired height value for each position of the surface. This new reference signal is also recorded in the memory of the control unit 46.

Figure 4:
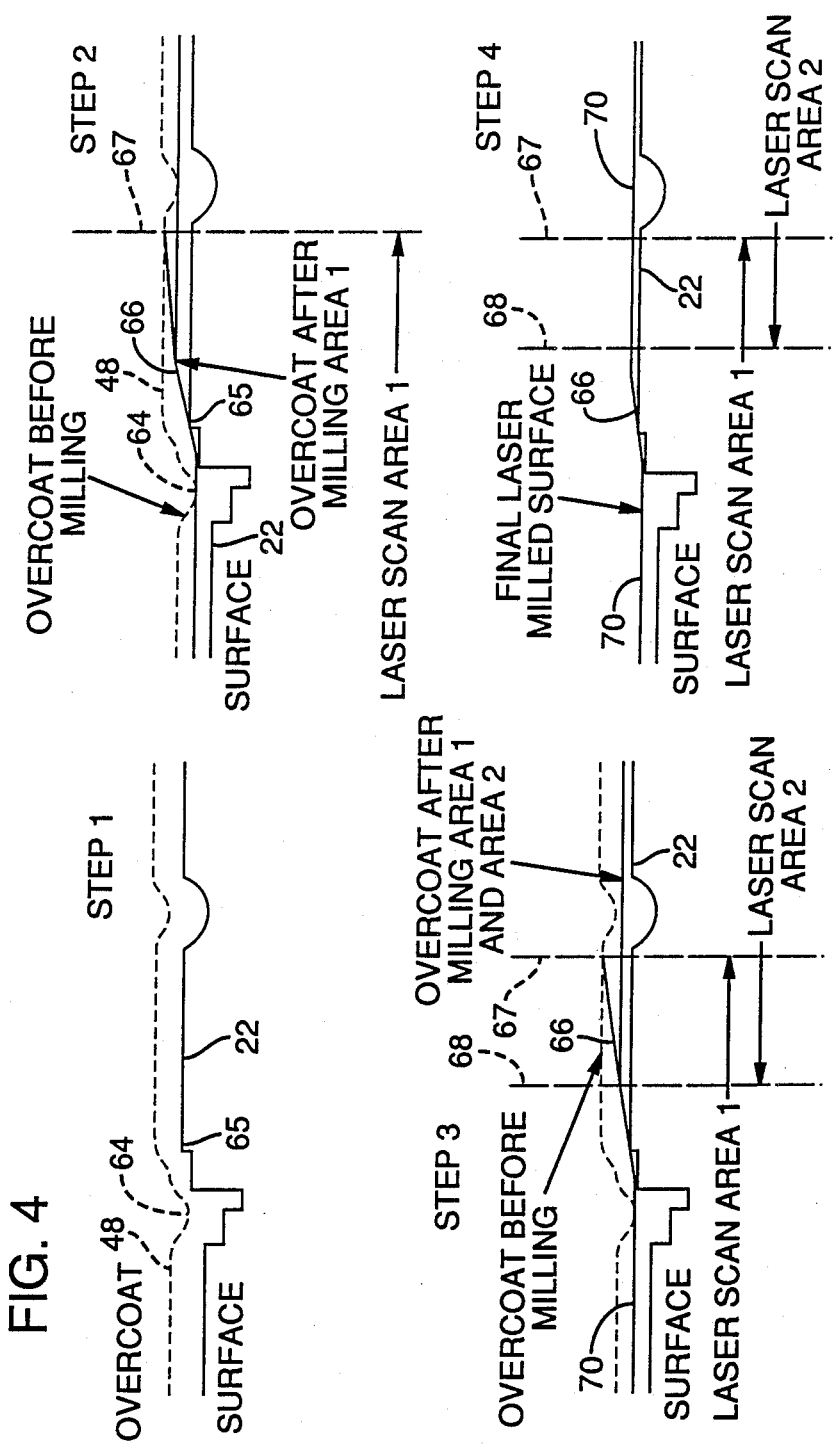
FIG. 4 is a conceptual drawing of a profile of an area to be milled, showing the method and successive steps of overcoating and laser milling to a preselected smoothness.

As shown in FIG. 4, after the surface 22 has been premapped it is then coated with an ablatable material 48 to a height sufficient to permit a milling off of the excess coating until the desired surface characteristics, within selected smoothness limits, are reached.

The coated surface 48 is now ready to be milled using the structured light mapping system 14 as a real-time feedback control mechanism in conjunction with the control system 46, for directing the laser 11. In this mode, the robotic system 26 positions the end effector 34 over a predetermined section of the surface 22.

By scanning the coated surface several positions ahead of the laser 11, the mapping system 14 generates in real time a new electronic signal representative of the topology of the coated surface.

Figure 6:
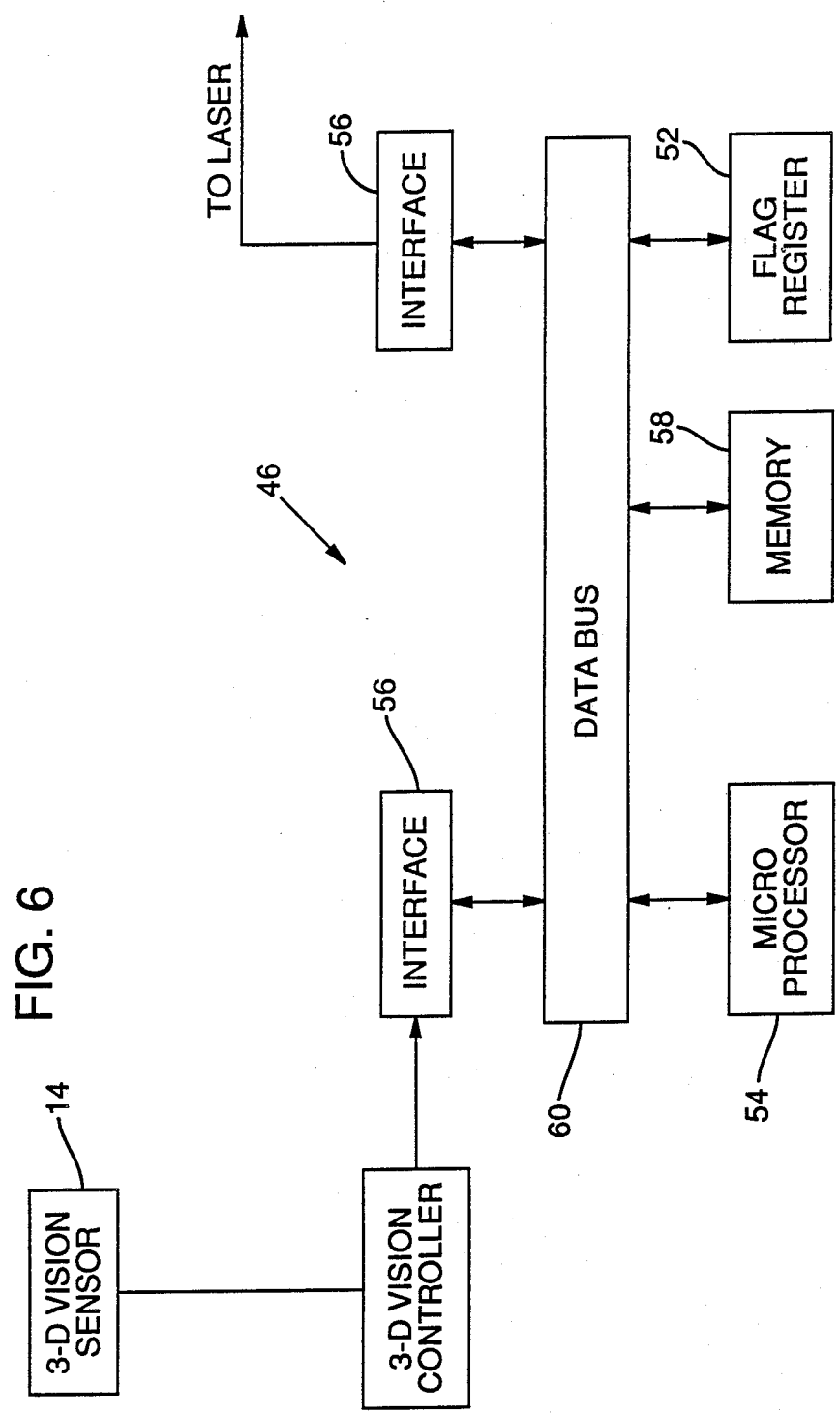
FIG. 6 is a block diagram of electronic elements which may be included in a control subsystem in a preferred embodiment of the invention.

The newly generated electronic signal is coupled to the control system 46 for comparison to the previously recorded reference signal representing desired surface profile. The results of the comparison are recorded by a flag register 52, indicated in the block diagram of FIG. 6. The register 52 has one flag for each square centimeter beam footprint unit within the scan area. A comparison indicating that the height value of the signal currently generated is above the relative height value of the stored reference signal will activate a "burn flag" for that particular footprint unit. A substantial match between the two signals would indicate that the surface is at the desired level and no "burn flag" will be set. A comparison which discloses that the point represented by the newly generated signal is below the relative reference point, or which indicates that any further milling will expose the substrate (when the preprogrammed criteria specifies the substrate is not to be exposed), will result in no burn flag being set and the position marked in order to bring it to the operator's attention.

A microprocessor (54 in FIG. 6) will then check the status of the flag register 52 with the results then communicated to the laser 11 through an appropriate interface 56 to control each raster of the laser beam 20 within the laser scan area 24. If any burn flags are found the control system 46 will cause the laser 11 to fire at the corresponding position. While the laser is executing the firing orders from the control system, the mapping system 14 will be farther ahead in the scan, to set the controller flag register 52 for footprints farther ahead.

Figure 7:
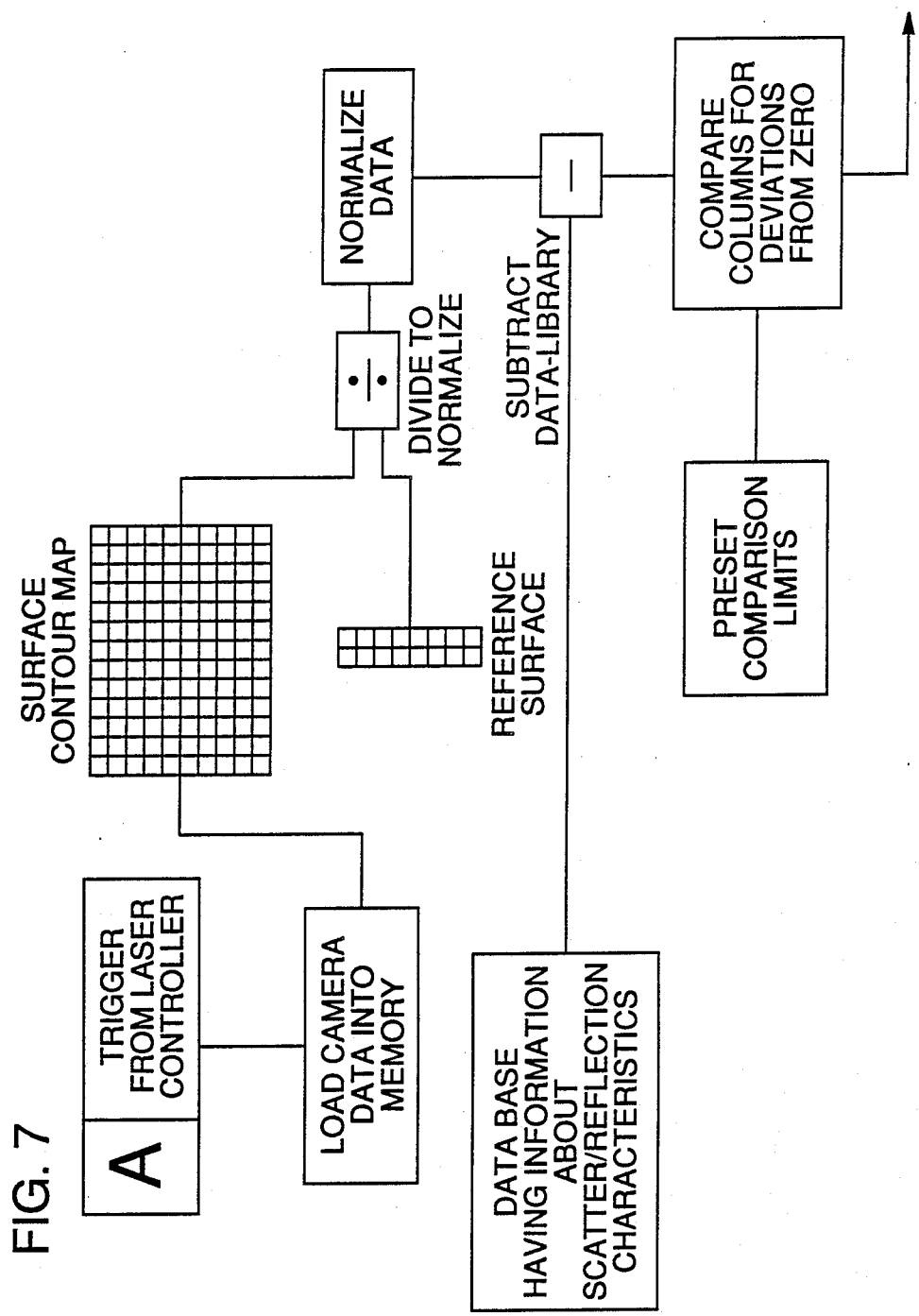
FIG. 7 is a more detailed block diagram of a portion of what is indicated in FIG. 5.
Figure 8:
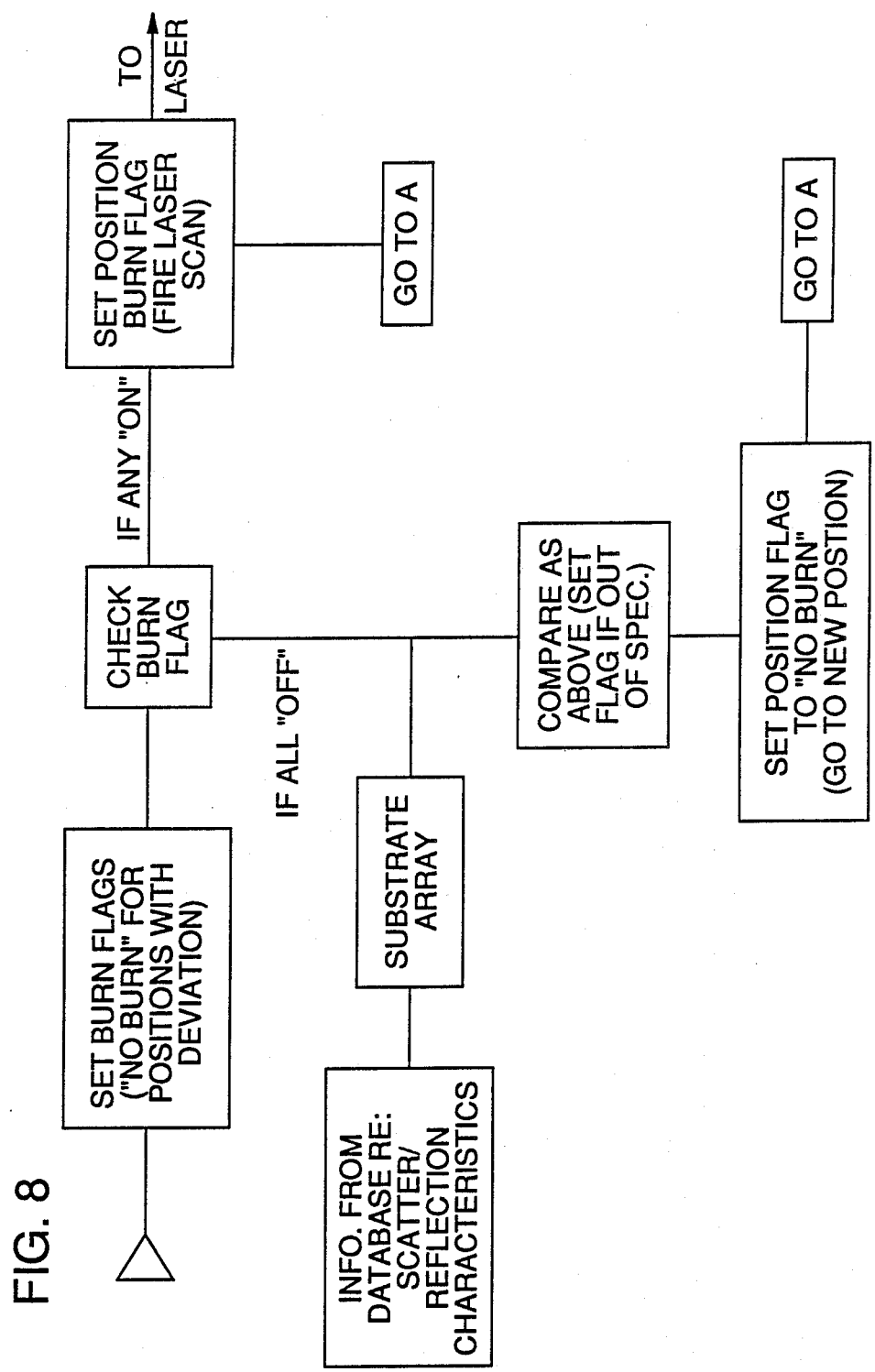
FIG. 8 is a flow chart illustrating a part of the process of the invention.

Upon initial start-up and at the end of each laser pulse according to this embodiment, a trigger signal is applied to a Point A (FIG. 7). The trigger signal causes the electronic signals from each data coordinate point to be loaded into the memory 58 in preparation for comparison by the control unit 46.

While the laser beam 20 is milling the position just scanned, the mapping system indexes to a subsequent raster scan position and collects new data relative to surface height for that position. The control unit again compares the height value of the generated signal with the height value of the reference signal at that position and makes a decision whether to fire the laser when the laser reaches that position in its raster. After the laser has completed milling of a scan area, the mapping system again scans the surface in real time to give an updated map to the control unit for determining the firing orders to be executed by the laser. This procedure continues across an entire frame until the surface features fall within the prescribed limits.

Any areas which are not within the program specification but which the laser cannot further mill because of the substrate being exposed or the overcoat surface already being below desired profile or other problems, will be noted by the control unit or system 46 and referred to the operator. The robotic laser milling and structured light mapping system are then moved to the next raster pattern area and the process begins again.

Structured light mapping systems are available commercially such as the Technical Arts Scanner 100X. Other three-dimensional vision systems could also be utilized to provide the necessary feedback signal such as holography, spectral interferometry, and laser backscatter. Each of these techniques has various advantages and disadvantages including flexibility, cost, reliability, accuracy and risk.

The laser backscatter will not provide as much detail as the holographic system, but it will generate sufficient information to smooth the surface at a reasonable cost. Such a system consists of a scanned laser using a spot similar to the laser milling footprint size. The beam is scanned over the laser raster area and a solid state camera detects the scatter from the surface at several angles. The computer then correlates the scatter detected at each angle with the known position of the laser at that time to determine the profile of the surface Also, an ultrasound mapping system may be employed to control the milling process where a specific thickness or other characteristic of the surface coating is desired, or in general for the same purposes as described above. With this method, the ultrasound determines the thickness of the coating on top of a substrate by measuring differences in ultrasound waves reflected off the surfaces of both the coating and the substrate. Once the thickness of the coating is determined, the control system is then able to determine the amount of material to be removed in order to reach the desired surface characteristics and sends firing instructions to the laser. This method does not require any premapping of the surface and also may operate as a real time feedback system responding to pre-programmed specifications.

The ultrasound mapping system not only has the advantage of eliminating the need to premap the surface prior to applying the coating. It also is advantageous in operating as a real-time feedback control system in which the entire mapping and milling sequence takes place in all respects simultaneously. Accordingly, there is no need to accommodate for variations and changes between the surface being milled and the milling system as is necessary when a system is premapped.

A raster beam subsystem, as explained above, provides the mechanism by which the laser beam is scanned over the surface and also provides means by which the raster pattern is shifted for each laser milling sequence to eliminate overlap. A series of sequentially shifted raster patterns, overlapping footprints, and exemplary energy distribution are shown diagrammatically in FIGS. 3A and 3B. The shifting of the raster pattern achieves a smooth surface without discernible steps normally expected due to the finite size of the laser beam.

In most applications this is an important feature and is made possible by taking advantage of the small incremental milling capacity of the laser. Should the laser beam have a very square profile and should the overlap of the laser footprint from one spot to the next not be precise, then a ridge of the material would be left where the laser had not removed it. Likewise, should two of those adjacent positions overlap, then the common area will have more material removed than either of the two adjacent areas.

Both of these are undesirable features and can be avoided using a two dimensional raster system. The raster takes advantage of the fact that in most milling operations, from 5 to 100 pulses are required for each footprint area to remove the desired amount of material. If the center position of each of the laser footprints in a raster is shifted slightly from one scan to the next then a smoothing takes place.

Figure 3:
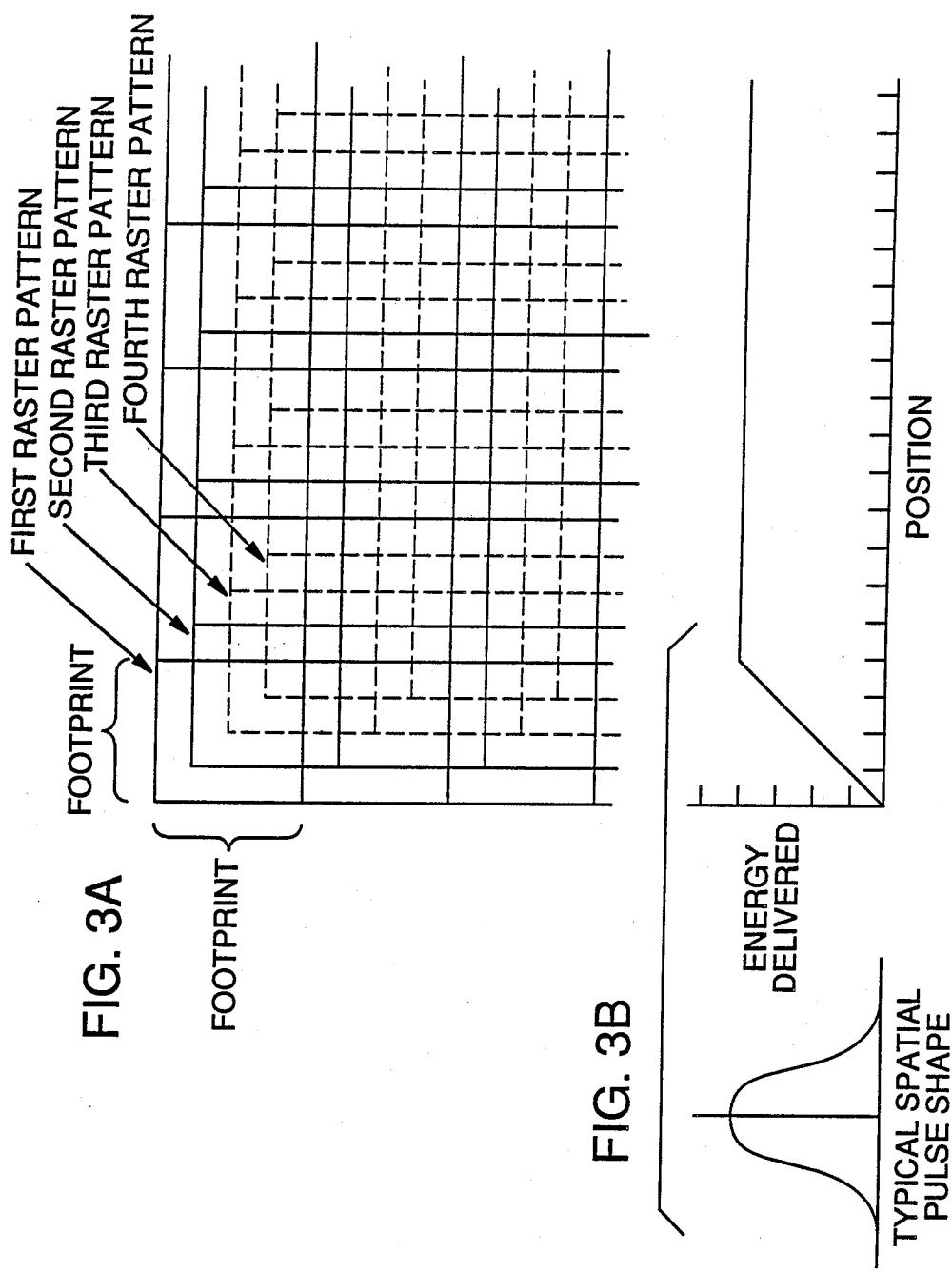
FIGS. 3A and 3B are diagrammatic and graphic representations illustrating successive offset beam rastering scan patterns used with the invention, with FIG. 3B showing laser energy delivered as a function of position.

As shown in FIG. 3A, this technique allows the total energy delivered to a area to be smoothed out even with a severe laser beam profile such as a truncated Gaussian, indicated in FIG. 3B. With proper rastering, severe beam profiles can be translated into only a few percent error in the total energy delivered to the work area. FIG. 3B indicates an even distribution of energy in the profile graph on the right, for all areas of full overlap, i.e. other than the edges of the scan area. This assumes firing at every spot.

FIG. 4, briefly mentioned above, shows the merging of two adjacent laser scan areas in accordance with the invention, as well as indicating successive steps of the process, as Step 1, Step 2, Step 3 and Step 4.

In Step 1, an irregular substrate surface profile 22 is shown by a solid line, with the overcoat 48 of ablatable material shown by a dashed line. The overcoat 48 is milled in successive overlapping sections corresponding to successive laser scan areas.

In Step 2 Laser Scan Area 1 is milled according to preprogrammed specifications from the control unit, which may ordinarily call for a flat surface where possible and a 20:1 slope, for example, extending between flat areas where a flat surface is not possible. In Step 2 it is shown that the profile of the substrate surface 22 in this example prevents the laser from milling the area completely flat without taking away a portion of the underlying substrate, or without a thicker overcoat being applied. This is because a valley 64 in the overcoat is lower than a point 65 on the substrate. Therefore the remaining portion 66 of Laser Scan Area 1 is milled at a 20:1 slope (or another prescribed criterion) to the outside of the frame or scan area, meeting the unmilled overcoat profile at the boundary 67 of Scan Area 1. The unmilled profile must be met at boundaries, since the system does not "know" that the overcoat at this point in the next scan area can be milled to any significant degree.

Step 3 shows the effect of the overlapping of Laser Scan Area 2 onto a part of the previously milled Laser Scan Area 1. The raster pattern results in a further milling of excess material so that an increased amount of Laser Scan Area 1 is milled flat. At the boundary 68 of Scan Area 2, the final milled surface meets the level already milled in Area 1 at that point.

Step 4 shows the final laser milled surface 70 in relation to the substrate surface 22.

The above described preferred embodiment is intended to illustrate the principles of the invention, but not to limit its scope. Other embodiments and variations to this preferred embodiment will be apparent to those skilled in the art and may be made without departing from the scope of the invention as defined in the following claims.

What is claimed is:

1. A method for selective and controlled removal of ablatable material from a surface on a substrate in order to achieve a desired surface contour, comprising the steps of:
   (a) premapping a given area of the substrate and generating a premap electronic signal representative of the three dimensional topography of the given area,
   (b) electronically generating and storing a reference signal representative of a desired topography of said given area,
   (c) applying a coating of an ablatable material on the given area to a height sufficient to permit a milling off of excess coating until the desired surface topography is reached,
   (d) while scanning said given area, generating a coated surface electronic signal representative of the three dimensional topography of the coated surface for each of a series of scan locations in the given scan area,
   (e) electronically comparing the coated surface electronic signal with the stored reference signal and, upon a comparison indicating the surface height of the coating is above the desired finished surface height for a given scan location as represented by the reference signal, impinging a high intensity beam of radiant energy on the coating at that scan location for a given period of time to achieve a milling of the surface; and
   (f) after said given period of time, comparing another coated surface electronic signal representing the topography of the newly milled surface and again impinging the beam of radiant energy on the given scan location for the given period of time only upon a comparison indicating the surface height of the coating is above the desired surface height for that location, and
   (g) repeating step f in repeated scans of the given area, until the electronic comparison indicates the mapped surface substantially matches the desired surface characteristics as represented by the stored reference signal.

2. The method of claim 1, wherein said reference signal is generated by applying preselected criteria regarding desired surface characteristics to said electronic signal representative of the three dimensional topography of said given area.

3. The method of claim 1, wherein said electronic signal representative of the 3D topography of said surfaces is generated by a structured light system.

4. The method of claim 3, wherein said structured light system comprises:
   (a) a low powered laser beam scanning system that provides a line of laser light across the surface to be mapped; and
   (b) a solid state camera at an angle and location fixed relative to the line of light such that the line of light reflected from the surface intersects the raster scan of said camera.

5. The method of claim 1, wherein said electronic signal representative of the 3D topography of said surfaces is generated by a laser backscatter mapping system.

6. The method of claim 1, wherein said high intensity beam is further controlled by a fine pointing and control subsystem.

7. The method of claim 6, wherein the fine pointing and control subsystem comprises a structured light pattern generated from a low-powered rotating laser beam forming a cone at the surface when the system is at the correct focal distance.

8. A method for selective and controlled removal of ablatable material from a surface in order to achieve a desired surface contour, comprising:
   providing a laser source and positioning a laser beam delivery means adjacent to the surface with the delivery means including scanning means for scanning a scan area of the surface in accordance with a selected scanning pattern;
   providing, in association with the laser beam delivery means, a surface mapping system for determining the actual contour of the surface at each of a series of sequential scan locations corresponding generally with the scanning pattern for the laser beam;
   providing a computer means with computer-stored information relating to a desired final surface contour for the surface, after milling by the laser;
   scanning both the laser beam and the surface mapping system over the scan area repeatedly, and, for each scan location, flagging that location in a computer system means for either "burn" or "no burn", as an instruction to the laser beam delivery means to either fire or not fire the laser at that scan location when the laser beam next reaches that location;
   firing the laser beam in accordance with such instructions and repeating this process through successive scans of the scan area, until the desired surface profile has substantially been achieved at each scan location in the scan area;
   and wherein the ablatable material is coated over a substrate which is not to be milled, and the method further including
   premapping the substrate surface in the scan area prior to coating the substrate with the ablatable material, to determine the surface contour in the scan area,
   storing data representing the substrate surface contour in the computer means,
   applying the coating of ablatable material to a sufficient thickness to permit a milling off of excess coating to achieve the desired final surface contour, and
   applying preselected, prestored criteria relating to permissible surface slopes to the stored data to compute said stored information representing the desired final surface contour.

9. The method of claim 8, wherein the mapping system is a laser backscatter mapping system.

10. A method for selective and controlled removal of ablatable material from a surface in order to achieve a desired surface contour, comprising:
   providing a laser source and positioning a laser beam delivery means adjacent to the surface with the delivery means including scanning means for scanning a scan area of the surface in accordance with a selected scanning pattern;
   providing, in association with the laser beam delivery means, a surface mapping system for determining the actual contour of the surface at each of a series of sequential scan locations corresponding generally with the scanning pattern for the laser beam;
   providing a computer means with computer-stored information relating to a desired final surface contour for the surface, after milling by the laser;
   scanning both the laser beam and the surface mapping system over the scan area repeatedly, and, for each scan location, flagging that location in a computer means for either "burn" or "no burn", as an instruction to the laser beam delivery means to either fire or not fire the laser at that scan location when the laser beam next reaches that location;
   firing the laser beam in accordance with such instructions and repeating this process through successive scans of the scan area, until the desired surface profile has substantially been achieved at each scan location in the scan area;
   and wherein the ablatable material is coated over a substrate which is not to be milled, and the method further including
   premapping the substrate with said mapping system prior to flagging "burn" and "no burn" on the scan locations to determine substrate surface contour, and
   computing said stored information representing desired final surface contour by applying preselected, prestored criteria relating to permissible surface slopes to information on the substrate profile determined by said premapping, to generate said stored information representing desired final surface contour.

11. The method of claim 10, wherein the premapping step includes using an ultrasonic mapping system which will determine both the contour of the ablatable material's surface and the substrate, to produce said information on the substrate profile.

12. Apparatus for selective and controlled removal of ablatable material from a surface coated on a substrate in order to achieve a desired surface profile, comprising:
   (a) means for premapping a scan area of the substrate and generating a first electronic signal representative of the three dimensional topography of the substrate,
   (b) means for electronically generating a second, reference electronic signal representing a desired final surface profile topography, in accordance with preselected criteria relating to permissible final surface slope and in accordance with the substrate topography as represented by the first electronic signal,
   (c) means for electronically storing the second reference signal, (d) means for scanning the surface of the ablatable material and for generating and storing a third electronic signal representative of the three dimensional topography of the coated ablatable material surface at each of a series of scan locations within the scan area, (e) means for electronically comparing the third electronic signal with the second, reference electronic signal for each scan location within the scan area, (f) means for impinging a high intensity beam of radiant energy, for a given period of time, on each scan location when the comparison of the third and second signals has indicated that the surface height of the coating is above the desired finished surface for that location as represented by the second, reference electronic signal, and (g) means for repeatedly scanning the scan area and, following the comparison of step e) for a scan location, for either impinging the high intensity beam or not impinging the beam at that scan location, based on the comparison, until the surface of each scan location substantially meets the height of the desired final surface topography for that location as represented by the electronic signal.

13. The apparatus as claimed in claim 12 wherein said means for impinging a high intensity, beam of radiant energy on said area for a given period of time comprises a $CO_2$ laser providing a pulse of radiant energy at a wavelength of about 10.6 microns and a pulse length of about twenty microseconds.

14. The apparatus as claimed in claim 12, wherein said means for generating the first electronic signal representative of the topography of the substrate comprises a structured light mapping system.

15. The apparatus as claimed in claim 12, wherein the means for generating the first electronic signal comprises a laser backscatter system.

16. The apparatus as claimed in claim 12, further comprising a rastering means for rastering said beam over a raster scan pattern.

17. The apparatus as claimed in claim 16, wherein said rastering means shifts said rastering pattern slightly for subsequent passes of the beam.

* * * * *